US005954049A

United States Patent [19]

Foley et al.

[11] Patent Number: 5,954,049

[45] Date of Patent: Sep. 21, 1999

[54] EQUINE MASK WITH MDI ADAPTER

[75] Inventors: Martin P. Foley; David Jenkins, both of London, Canada

[73] Assignee: Trudell Medical Limited, Canada

[21] Appl. No.: 07/947,821

[22] Filed: Sep. 24, 1992

Related U.S. Application Data

[63] Continuation-in-part of application No. 07/776,835, Oct. 15, 1991, abandoned.

[51] Int. Cl.[6] .......................... A61M 16/00; A61M 11/00; A61M 15/08; F16K 11/00

[52] U.S. Cl. ................................ 128/203.29; 128/200.23; 128/203.23; 128/203.25; 128/200.24; 128/204.11; 128/204.12

[58] Field of Search ......................... 128/200.14, 200.18, 128/200.21, 200.23, 200.24, 203.12, 203.25, 203.29, 204.11, 204.12, 204.14, 206.21, 206.24, 206.26–206.28, 203.23

[56] References Cited

U.S. PATENT DOCUMENTS

| | | | |
|---|---|---|---|
| 2,843,119 | 7/1958 | Glasser | 128/206.26 |
| 3,491,755 | 1/1970 | Barghini et al. | 128/207.13 |
| 4,002,167 | 1/1977 | Rambosek | 128/205.25 |
| 4,470,412 | 9/1984 | Nowacki et al. | 128/200.23 |
| 4,546,768 | 10/1985 | Ferierabend | 128/200.16 |
| 4,722,334 | 2/1988 | Blackmer et al. | 128/203.16 |
| 4,886,055 | 12/1989 | Hoppough | 128/203.28 |
| 5,012,803 | 5/1991 | Foley et al. | 128/200.23 |
| 5,012,804 | 5/1991 | Foley et al. | 128/200.23 |
| 5,062,423 | 11/1991 | Matson et al. | 128/207.15 |

FOREIGN PATENT DOCUMENTS

| | | | |
|---|---|---|---|
| 244490 | 11/1993 | Argentina . | |
| 336052 | 2/1904 | France | 128/201.23 |
| 815329 | 5/1937 | France | 128/206.21 |
| 2481122 | 10/1981 | France | 128/206.24 |
| 726282 | 10/1942 | Germany | 119/1 |
| 3000518 | 7/1981 | Germany | 128/206.21 |
| 531805 | 1/1941 | United Kingdom | 128/206.12 |

*Primary Examiner*—Kimberly L. Asher

*Attorney, Agent, or Firm*—Brinks Hofer Gilson & Lione

[57] ABSTRACT

A mask is provided for administering medication, particularly asthmatic medication, to equine animals, particularly horses. The mask has a body that fits over the nostrils of the horse. An aerosolization chamber is secured to the body and opens into the interior thereof, and is supplied with misted medications such as from a metered dose inhaler, for inhalation by the animal. The mask and body is also provided with one or more exhalation ports, and a strap or band or the like for securing the body to the animals face overlying the nostrils.

19 Claims, 10 Drawing Sheets

EQUINE MASK WITH MDI ADAPTER

RELATED APPLICATION

The present application is a continuation-in-part of prior application Ser. No. 07/776,835, filed Oct. 15, 1991, now abandoned, by the same inventors, entitled "EQUINE MASK".

BACKGROUND OF THE INVENTION

Many people suffer breathing problems, particularly asthma, from allergic reactions. Asthma is frequently triggered by grasses, grains, and dust. Alternatively, wet materials, particularly molds often trigger asthmatic attacks. Much work has been done to ameliorate asthmatic attacks in human beings. Metered dose inhalers (MDI) have been developed which will deliver a metered does of medication upon depression of an outlet valve. Epinephrine was one of the first such anti-asthmatic drugs to be packaged in metered dose inhalers. However, epinephrine has undesirable side effects, and better medications have been developed, such as metaproterenol, and albuterol. These have a more direct action on the bronchi and do not have nearly as many side effects.

The metered dose inhalers do not themselves produce a sufficiently aerosolized form of medication to be highly effective. Various efforts have been made to provide chambers between the metered dose inhalers and the users, say for example Nowacki et al U.S. Pat. No. 4,470,412, and Foley et al U.S. Pat. No. 5,012,803. The aerosolizing chambers disclosed and claimed in the two foregoing patents are relatively inexpensive and highly effective in producing more efficient use of the medication.

There is another class of sufferers of asthma that has not as yet been given adequate attention. Members of the equine family often suffer from asthma. For example, it is estimated that there are 10,000,000 horses in the United States. It is further estimated that 60% of the horses are asthmatic. This means that there are something on the order of 6,000,000 asthmatic horses in the United States alone. Although prospectively one does not tend to think of horses and other animals of the equine family as being sufferers of asthma, it would be appreciated that such animals are constantly around grasses, grains, dust, molds, etc. which are recognized allergens. The problem is particularly acute with horses that have to perform physically, such as race horses, working farm horses, etc. Some little work has been done with nebulizers, but these have not been very effective. Furthermore, it is believed that there is no anti-asthmatic medication with special efficacy in the equine family. Further, it is believed that it will be many years before any such specific anti-asthmatic medication is developed. However, we have found that human type anti-asthmatic medications are effective with horses and the like.

The problem is to deliver anti-asthmatic medication to equine animals. It is true that horses can be taught some tricks, and certain working activities, but there is no evidence to indicate that a horse can be told when to inhale, and when to hold its breath, etc.

OBJECTS AND SUMMARY OF THE PRESENT INVENTION

It is an object of the present invention to provide a delivery system for supplying asthmatic medication to members of the equine family.

More particularly, it is an object of the present invention to provide an equine mask cooperable with a modular medication inhaler as disclosed and claimed in the aforesaid Foley et al U.S. Pat. No. 5,012,803 for supplying anti-asthmatic medication to equine animals.

Further objects include the provision of a mask which is readily attached over the nostrils and mouth of an equine animal, which mask has provision for causing the animal to gasp, and thereby draw in more medication, and which mask further has a visible exhalation valve so that one may observe the breathing pattern of such an animal.

In carrying out the foregoing and other objects of the present invention we take advantage of the fact that horses are accustomed to having devices placed over their mouths and adjacent portions of the head, feedbags being common examples. We provide a mask covering the nostrils and mouth of a horse which is lightly sealed to the adjacent areas of the horse's head, but allowing a certain amount of air to pass under the seal along the horse's mouth, as this is comforting to the horse; FIG. 21 is a view generally similar to FIG. 6, but showing a modification using a nebulizer rather than a metered dose inhaler; and FIG. 22 is a fragmentary view showing a modification of a portion of FIG. 21. Either the mask is readily attached to the horse or other equine animal by means of attachments secured to the normal harness of the horse, or by means of a strap, such as one embodying hook and loop fasteners (Viz., VELCRO). An aerosolizing chamber as previously noted in accordance with U.S. Pat. No. 5,012,803 is secured to the mask, preferably in a horizontal position for most effective distribution of the medication. Rubber flap exhalation valves are provided in the mask adjacent each nostril of the horse or the like, with the flaps of the exhalation valves readily visible so that the breathing pattern of the horse can be observed. The aerosolizing chamber is connected to the mask by a bypass passageway which enables the owner or veterinarian to control to some extent the inhalation of the horse or the like, thereby producing gasping to clear the airways, and to pull in the medication.

A knob canopy also is provided on the mask which is readily grasped by the hand of an owner or veterinarian in order properly to position the mask relative to the nostrils and the mouth of the animal.

THE DRAWINGS

The present invention will best be understood from the following specification when taken in connection with the accompanying drawings wherein.

DETAILED DISCLOSURE OF THE ILLUSTRATED EMBODIMENTS

A. First Embodiment (FIGS. 1–3)

Figure 1:
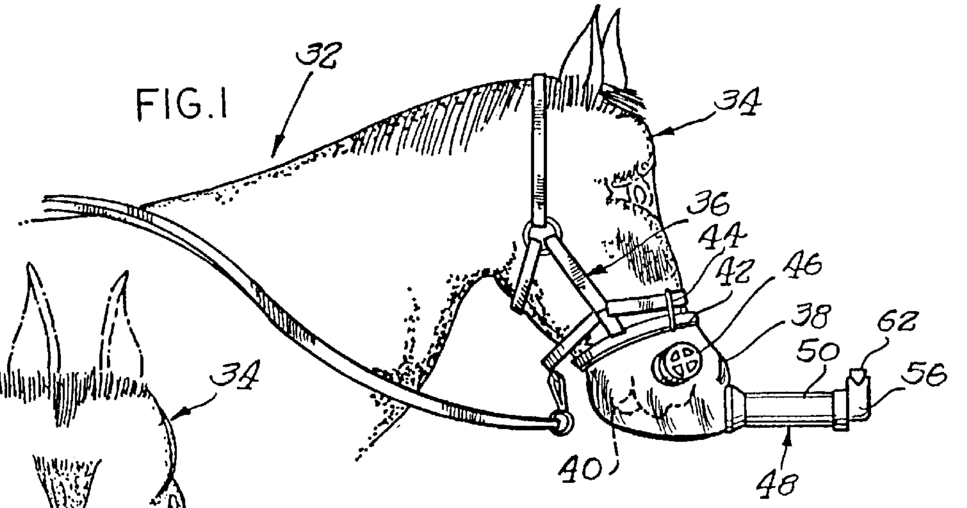
FIG. 1 is a side view of the front end of a horse with the mask, etc. of the present invention in place.
Figure 2:
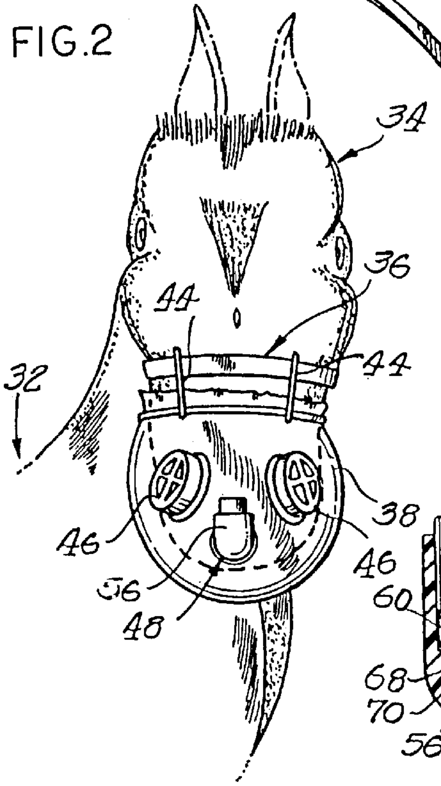
FIG. 2 is a front view of the horse and mask of FIG. 1 on a slightly enlarged scale.
Figure 3:
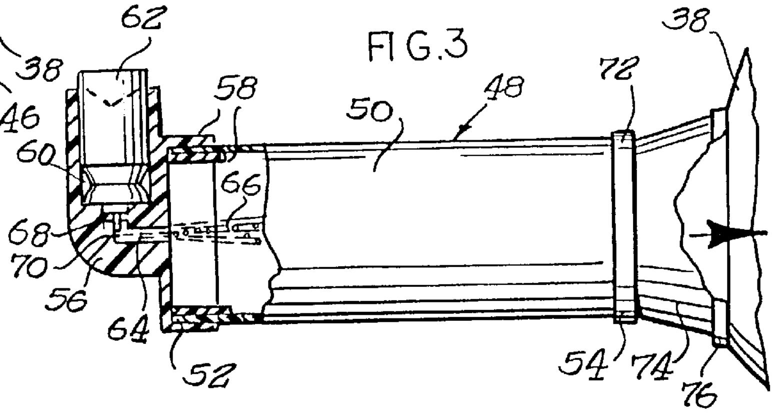
FIG. 3 is an enlarged side view partially in section of the metered dose inhaler and the aerosolization chamber.

Reference now should be made in greater particularity to the drawings, and first to FIGS. 1 and 2 wherein there is shown the front portion of a horse 32 including the head 34. A harness 36 of a conventional nature is applied over the horse's head. A mask or bag 38 is placed over the nostrils and over the mouth 40 of the horse. The mask 38 has a surrounding band 42 adjacent the upper edge thereof, and suitable links 44 are secured to this band and are received over a portion of the harness 36 to hold the mask in place. The band 42 is of the size to fit snuggly about the horse's head just above the mouth and nostrils, and the size may vary depending on the type of horse and the individual animal. The mask 38 may be molded resinous plastic material, and this may be reinforced with a cloth or webbing. The mask must be somewhat flexible, but it must also have sufficient rigidity to prevent collapse against the horse's nostrils upon inhaling.

The mask is provided with two one way exhalation valves 46. These may be flap valves for suitable external clearance to allowed outward flexing thereof upon exhalation, and backed by a spider to be closed upon inhalation. The valves 46 are respectively adjacent the horse's nostrils for minimum interference with exhalation.

A medication aerosolization inhaler 48 extends forwardly from the lower front portion of the mask 38, and communicates with the interior of the mask to permit inhalation by the horse of medication as the horse inhales. The construction of this inhaler is structurally substantially, and functionally identical with the inhaler shown in Foley et al U.S. Pat. No. 5,012,803. The inhaler 48 includes a cylindrical body 50 which has an open upstream, inlet or entering end 52, and a downstream or exit end 54. An inlet fitting 56 is secured to the inlet end 52 of the cylinder 50 by means of a concentric pair of cylindrical flanges 58 fitting respectively inside and outside of the entering end 52 of the body 50. The inlet fitting 56 includes a well 60 which receives a metered dose inhaler canister 62. The fitting includes a lateral passageway 64 for conducting medication 66 from the canister into the inhaler body 50. The lower end of the canister is provided with a nozzle 68 which impinges against a shelf 70. When the canister 62 is pressed down in the well 60 the nozzle 68 is relatively depressed and discharges a metered dose of the medication as indicated at 66.

At the outlet end 54 of the inhaler 48 there is an outlet fitting 72 which is structurally and functionally similar to the outlet fitting in the afforesaid Foley et al U.S. patent. A portion 74 of the mask 38 flares substantially conically outwardly from the fitting 72, and a surrounding ring 76 is provided where the flared portion 74 joins the remainder of the mask 38. The cylindrical body 50 of the inhaler is molded rigid plastic material, while the inlet fitting 56 and outlet fitting 72 are also molded of a suitable plastic material.

Alternatives for First Embodiment Inhaler Attachment

Figure 4:
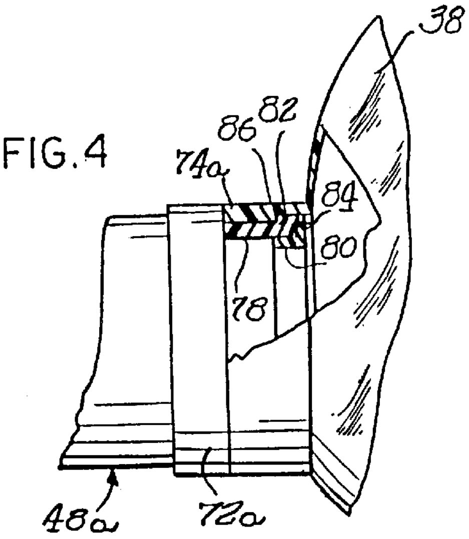
FIG. 4 is a detail of a modification of a portion of FIG. 3.

A modification of the attachment of the mask to the inhaler is shown in FIG. 4, this being very similar to what is disclosed in the aforesaid Foley et al U.S. patent. Certain other parts are the same as those here to afore disclosed, and identified with similar numerals with the addition of the suffix a. The outlet fitting 72 includes a cylinder extending in the downstream direction, and having secured at the downstream end thereof inner and outer flanges 80 and 82, respectively, interconnected by a radial web 84. The portion 74*a* at the front end of the mask 38 is cylindrical rather than flared, and has an internal diameter to fit over the outside of the cylindrical portion 78, being recessed at 86 to fit over the flange 82, whereby the mask is anchored to the inhaler.

Figure 5:
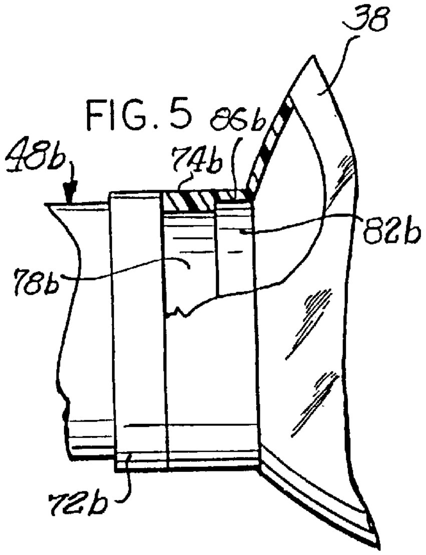
FIG. 5 is a detail similar to FIG. 4 of a further modification.

A further modification is shown in FIG. 5. Similar parts again are identified by like numerals, this time with the addition of the suffix b. In this instance there is an integral flange 82*b* preferably encircling the outlet end of the cylindrical wall 78*b*. The cylindrical portion 78*b* and 86*b* fits over the wall 78*b* and the flange 82*b* in the same manner as in FIG. 4.

B. Second Embodiment (FIGS. 6–9)

Another eariler preferred form of the invention is shown in FIGS. 6–9. The horse is identical, and portions of the invention are the same or similar to those heretofore shown and described, and in this instance are identified by like numerals with the addition of the suffix c.

The mask 36*c* is provided at the lower portion with a "dribble-section" or "slobbering cup" 88. Horses often sputter when relaxed, and this portion serves as a collecting place for sputtered saliva.

Figure 6:
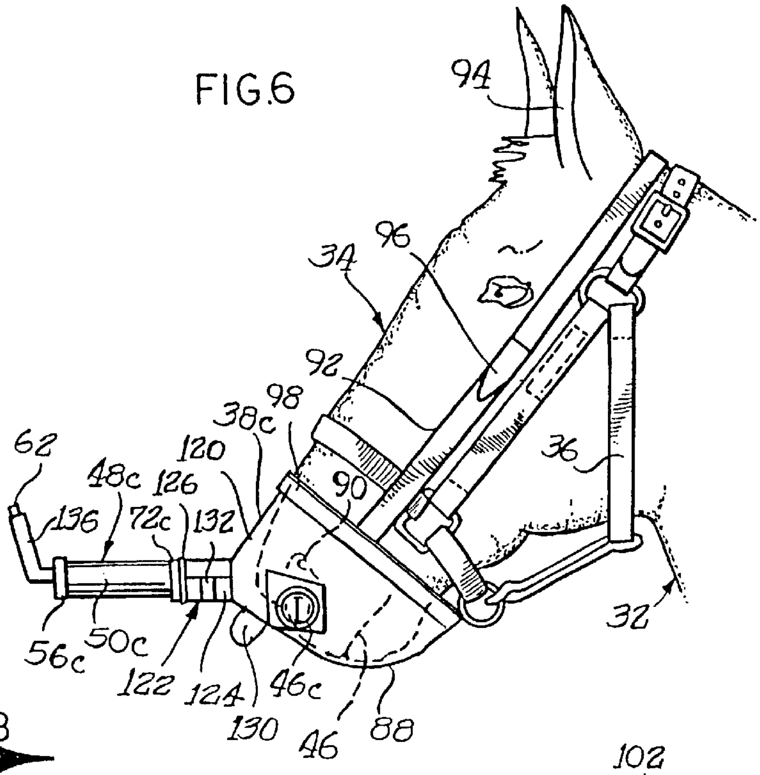
FIG. 6 is a view generally similar to FIG. 1 showing a preferred form of the invention.

The two exhalation ports 46*c* are lowered slightly from their position in FIGS. 1 and 2, whereby the nostrils 90 of the horse are visible in FIG. 6. A strap 92 extends from two discrete locations at the top edge of the mask 38*c,* passing behind the horse's head immediately behind the ears 94. The strap is provided with what might be called a buckle section 96, with opposing portions having hook and loop fasteners (Viz., VELCRO).

Figure 7:
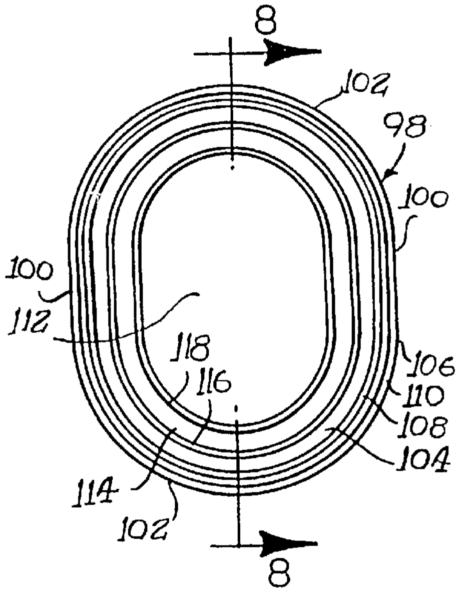
FIG. 7 is an axial view of the gasket for fitting the mask to the horse.
Figure 8:
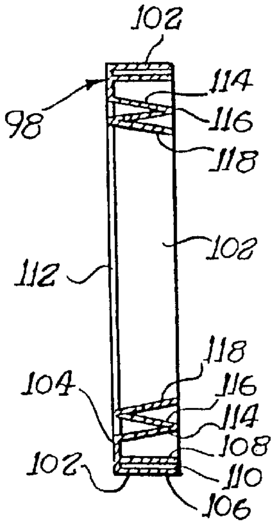
FIG. 8 is a sectional view through the gasket of FIG. 7 as taken substantially along the line 8—8 in FIG. 7.
Figure 9:
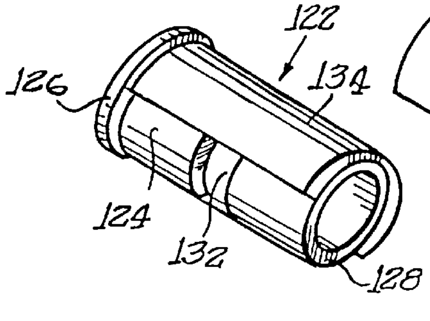
FIG. 9 is a perspective view of a supplementary inhalation device joining the aerosolization chamber to the mask.
Figure 9A:
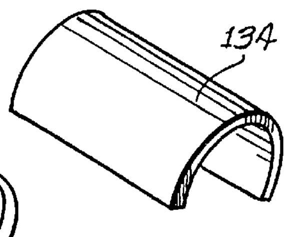
FIG. 9A is a perspective view of a portion of the supplementary inhalation area of FIG. 9.
Figure 9B:
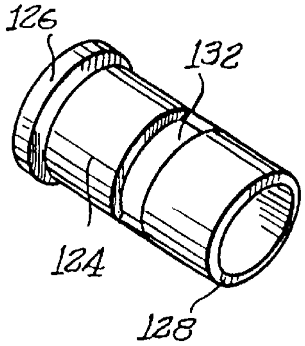
FIG. 9B is a perspective view of the remaining portion of the supplementary inhalation device of FIG. 9.

The upper edge of the mask is provided with a rubber seal or gasket 98 for connecting the mask to the horse. This seal or gasket is best seen in FIGS. 7 and 8, and in outline comprises generally straight side edges 100 interconnected at the top and bottom by arcuate portions 102. The seal includes a substantially flat transverse wall 104, which has a perpherial outer flange 106 extending at right angles from the wall 104. An inner perpherial flange 108 is parallel to the flange 106, and spaced inwardly therefrom a short distance, providing a gap therebetween at 110. The gap 110 receives the upper or rear edge of the mask, and the flanges 106 and 108 are adhesively or otherwise suitably secured to the mask on the outer and inner surfaces thereof, respectively.

The rubber seal 98 is provided with a more-or-less central opening shaped similar to the exterior of the mask, but shifted upwardly somewhat therefrom, whereby the wall 104 has a greater radial dimension at the bottom portion of the seal than it does towards the top. The opening 112 is defined by reentrant flanges 114, 116, and 118. The flanges, as seen in FIG. 8, form substantially a z-shape in section.

Considering FIGS. 7 and 8 along with FIG. 6, it will be seen that the innermost flange 118 of the re-entrant flanges presses against the horse's muzzle. The flange 118 lies across the rear portion of the mouth of the horse. This permits air flow through the cavities on either side of the horse's mouth, and this soothes the horse as air flows past.

The entering portion of the mask 38*c* is substantially bell shaped at 120, and is connected to the exit end of the aerosolization inhalation chamber by a supplementary inhalation area or device 122. The exit end fitting 72*c* of the chamber 48*c* is essentially the same as in FIGS. 4 or 5, and the supplementary inhalation device 122 includes a cylindrical body 124 with a perpherial flange 126 at the inlet end, the body fitting over the cylindrical portion of the exit fitting. A reinforcing portion 126 of the bell shaped entering portion of the mask 38*c* is suitably affixed to the rear end 128 of the cylinder 124, by adhesive or by other suitable means. The reinforcing portion 126 also supports a knob 130 extending below the supplementary inhalation device 122 to permit manual grasping thereof, and positioning of the horse's head. The body is provided at an axially midway position with an arcuate slot 132 of approximately 180 degrees, or possibly less.

A semi-cylindrical closure or cover member 134 extends from end to end of the body 124 and encircles the body over somewhat greater than 180 degrees, whereby to be retained on the body. The cover or closure member 134 is arcuately movable about the body to uncover substantially all of the slot 132, to totally close the slot 132, or to have it partially open.

The inlet fitting 56*c* in this instance is similar to that in the aforesaid Foley et al U.S. patent, and a substantially L-shaped adapter 36 receives the metered dose inhaler cartridge 62 for introduction of misted medication into the aerosolization inhaler.

When it is desired to introduce asthmatic medication into the horse's respiratory system, the owner or a veterinarian will watch the flap valves in the exhalation ports to note the horse's breathing pattern with the slot 132 open wide. Shortly after the completion of an exhalation the owner or veterinarian depresses the metered dose inhaler cartridge 62 to introduce a mist of medication into aerosolization chamber 46*c*. The cover or closure member 134 then is rotated to close the slot 132. This makes breathing somewhat difficult for the horse, and the horse inhales with a gasp, thus inhaling the now aerosolized medication. Breathing resistance tends to open up the horse's airways allowing for a more effective use of the medication.

As heretofore shown and described the medication aerosolization inhaler 48 is preferably used in a horizontal position, as this produces the best aerosolization and use of the medication. The specific form of the invention as shown in FIGS. 6–9 has proven by test to be the preferred form. It will be noted that the fit of the flanges on the horse's muzzle is with the rubber seal reversed from the position of the FIG. 8, whereby the taper of the flange 118 adapts well to the shape of the horse's nozzle. Additional embodiments of the invention that have been considered and/or tried are shown in the ensuing FIGS. 10–20.

C. Third Embodiment (FIG. 10)

Figure 10:
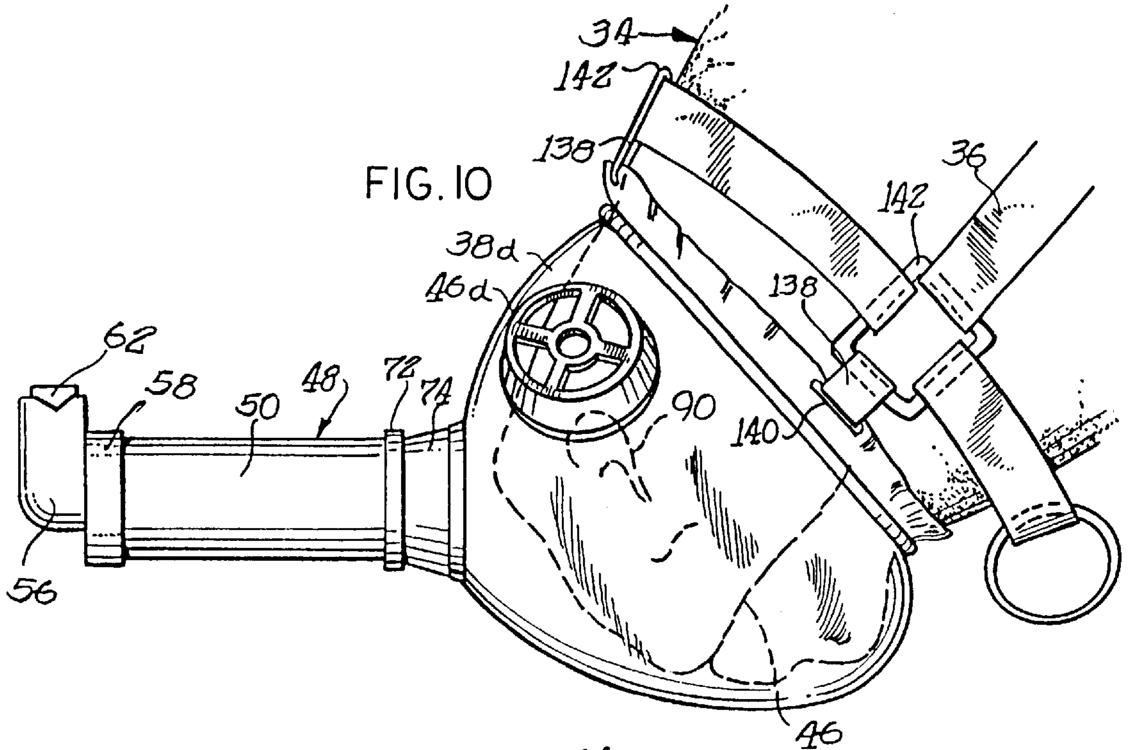
FIG. 10 is a fragmentary view of the front portion of the horse's head with a modification of the invention applied thereto.

An earlier form of the invention is shown in FIG. 10 which is generally similar to that shown in FIG. 1, et seq. Most of the parts are identical, and are identified with the same numerals. Where there are changes, like numerals are utilized with the addition of the suffix d. The mask 38*d* is secured on the horse in similar fashion, but with a strap 138 running from a slot 140 adjacent to the upper edge of the mask, the strap also being looped over a metal O-ring 142 forming a part of the harness 36. It will be understood that there is a plurality of such loops and rings. In addition, the exhalation ports 46*d* will be seen as positioned somewhat above the horse's nostrils 90. Although this position worked, the lower position shown in FIG. 6 is more effective in direct porting of the exhaled breath of the horse.

D. Fourth Embodiment (FIG. 11)

Figure 11:
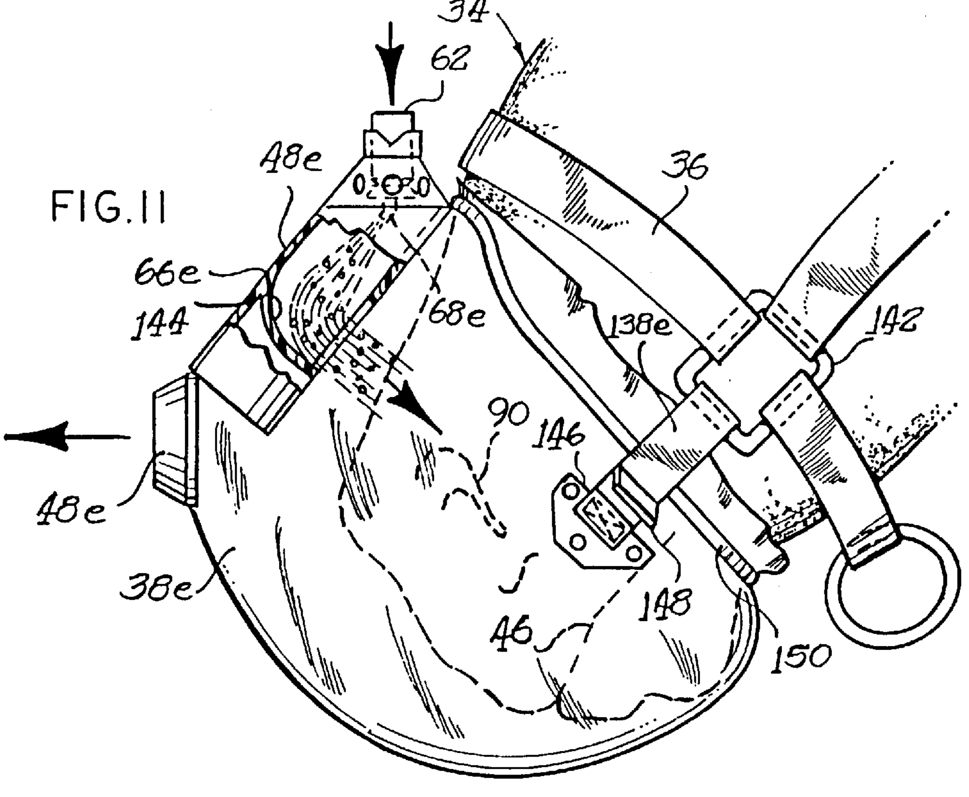
FIG. 11 is a view generally similar to FIG. 10, but showing a modification of the invention.

Another early embodiment of the invention is shown in FIG. 11. Again like numerals are used for identifying similar parts, this time with the addition of the suffix e. Distinctions reside in the provision of but a single exhalation port 48*e* at the front central portion of the mask 38*e*. Another distinction is that the aerosolization chamber 48*e* is actually built onto the top portion of the mask, and has a curved deflecting wall 144 therein for deflecting the medication 66*e* into the mask adjacent the horse's nostrils. The exit or valve member 68*e* is provided with a bend therein so that the initial discharge is axial of the aerosolization chamber 48*e,* which lies parallel to the upper front portion of the mask 38*e.* A further change is that an anchor 146 is provided on each side of the mask with a strap 138*e* thereon extending through the O-ring 142 on each side. The strap preferably is provided with a latching or buckle area 148 having opposed hook and loop fasteners (Viz., VELCRO). As in the embodiment of the FIGS. 1 and 2 and also FIG. 10, there is a band 150 encircling the upper portion of the mask to hold it in engagement with the frontal portion of the horse's head.

E. Fifth Embodiment (FIGS. 12 and 13)

Figure 12:
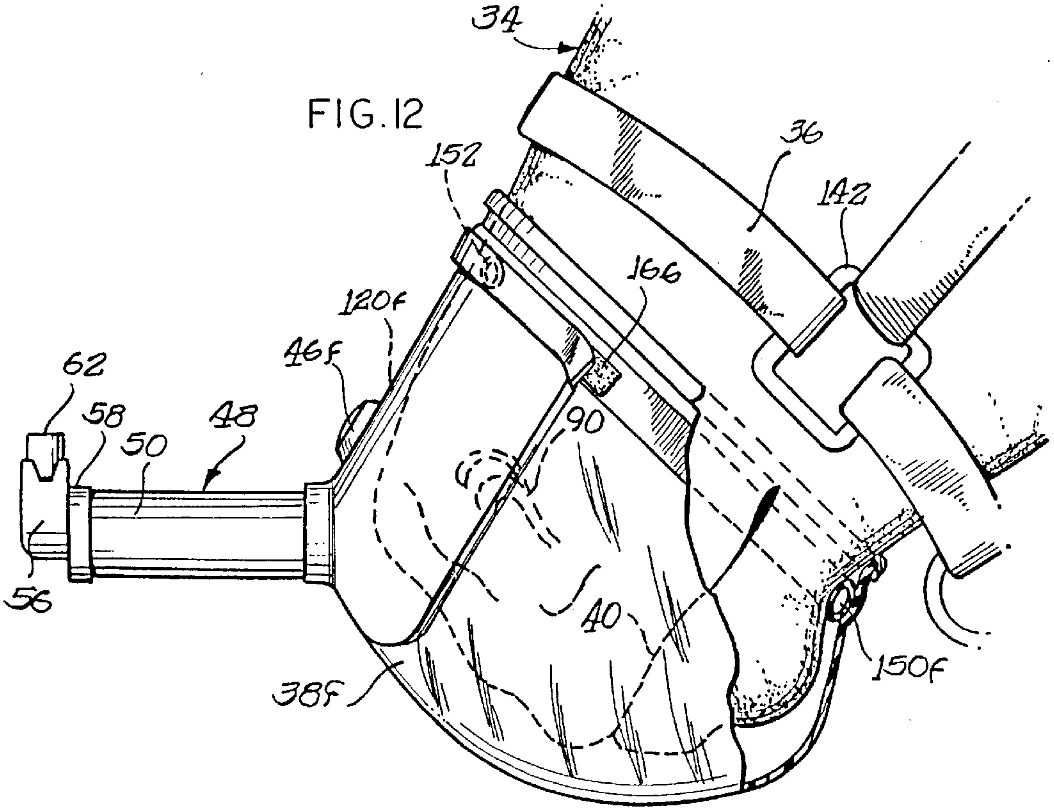
FIG. 12 is another view similar to FIG. 10 showing a further modification of the invention.
Figure 13:
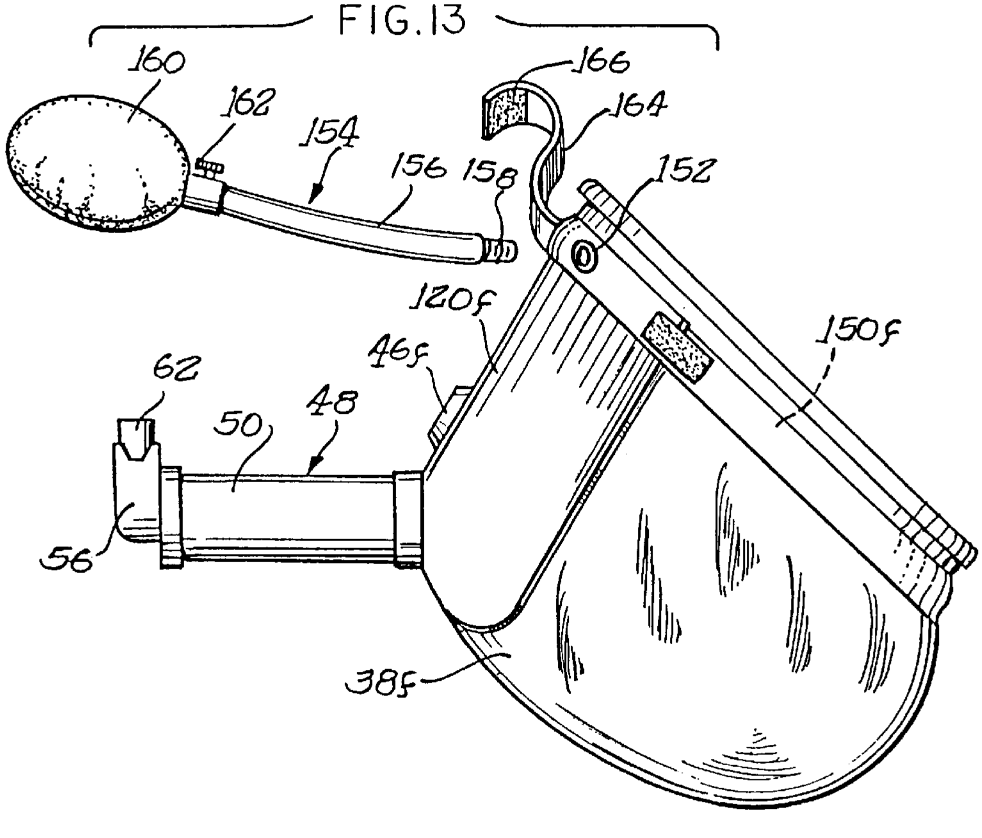
FIG. 13 is a view of the mask and cooperating parts of FIG. 12 showing an air bulb for blowing up the seal of the gasket to the horse.

A further embodiment of the invention is shown in the FIGS. 12 and 13. Generally, parts are similar to those heretofore disclosed, and similar parts are identified by the same or like numerals with the addition of the suffix f.

In this form of the invention there is a rather large central forward reinforcing area 120*f* secured to the mask, and which receives the aerosolization chamber, the same as in FIGS. 1–3, and similar to FIG. 6. There is a single exhalation port 46*f* on this reinforcing portion, aligned with the chamber 48 and somewhat above the nostrils 90.

The most significant distinction in this instance is that the mask is secured by clamping to the horse's head by a strap 150*f,* which specifically is a pneumatic tube. The tube initially is not inflated, and the mask is placed over the nostrils and mouth of the horse. An inlet valve 152 is provided for the pneumatic tube 158. An inflater 154 comprises a tube 156 with a threaded end 158 for threading into the inlet 152, and a pneumatic rubber bulb 160 at the other end, with a valve including a screw 162. The pneumatic tube is inflated to grip against the horse's muzzle, and a cover strip 164 covers the inlet valve 152, and is secured in place by hook and loop fasteners 166.

F. Sixth Embodiment (FIGS. 14–6)

Figure 14:
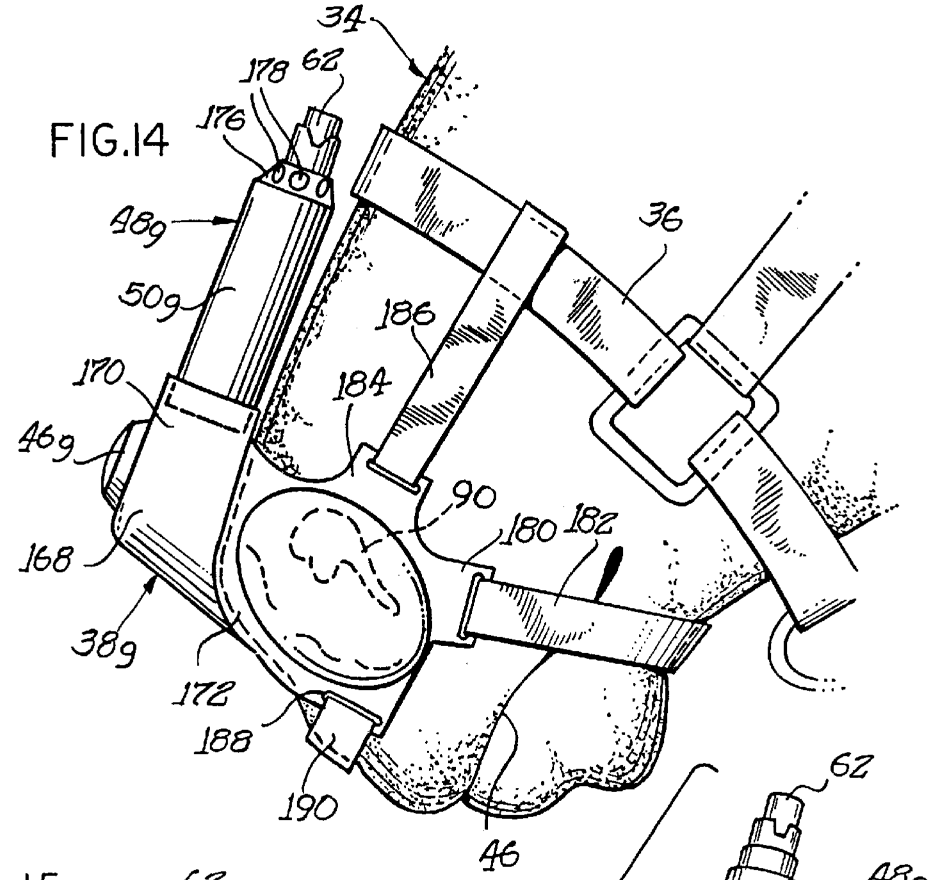
FIG. 14 is a view generally similar to FIG. 10 showing a modification of the invention applied only to the horse's nostrils, and with the mouth held shut.
Figure 15:
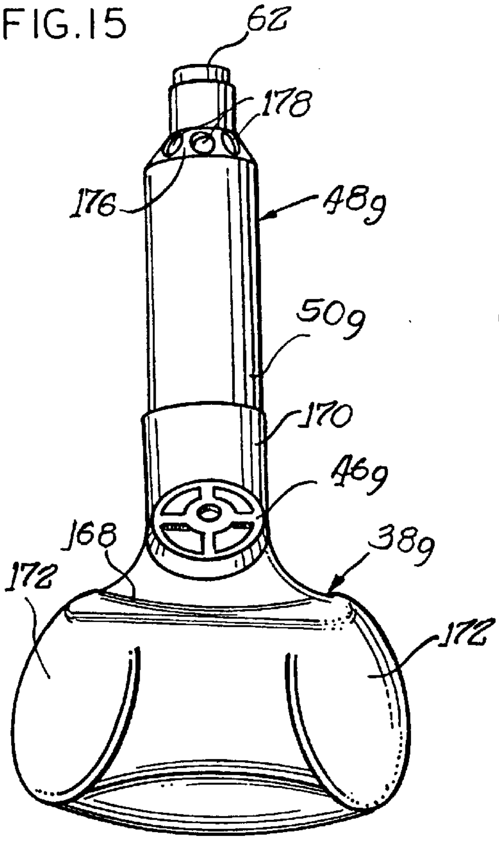
FIG. 15 is a front view of the invention as illustrated in FIG. 14.
Figure 16:
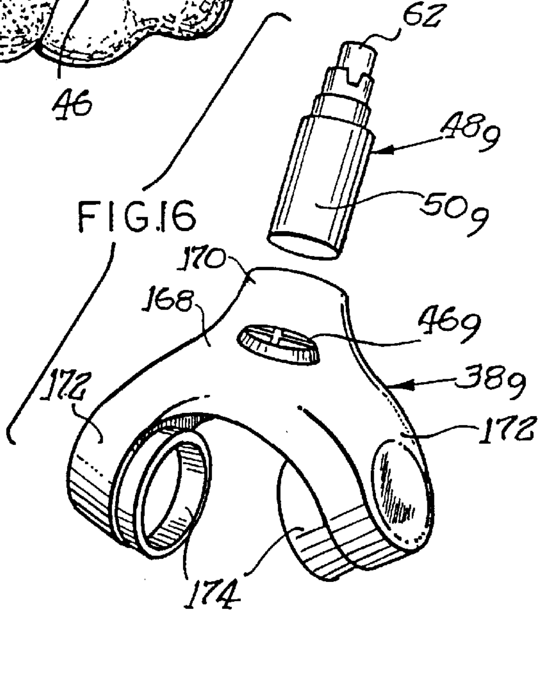
FIG. 16 is a top view form of the invention shown in FIG. 15.

A somewhat different form of the invention is shown in FIGS. 14–16. The numerals used for various portions of the horse and harness remain identical with those previously used. Insofar as portions of the mask are similar to those heretofore used, similar numerals are used with the addition of the suffix g. The form of the invention in FIGS. 14–16 is somewhat skeletonized compared with previous embodiments. Mask 38 includes a hollow body 168 with a tubular entrance end 170 extending thereinto. The cylindrical body 48*g* of the aerosolization chamber 50*g* plugs directly into the tubular entrance 170 of the hollow body 168. The single exhalation port 46*g* is mounted on the top or frontal portion of the hollow body. Hollow side branches 172 extend from the body to the vicinity of the horse's nostrils 90, and substantially cylindrical cups 174 extend therefrom to overlie the nostrils 90, thus establishing communication between aerosolizing chamber 50*g* and the horse's nostrils. Exhalation is through the cups 174 and the hollow body 168 to the exhalation port 46*g*. It will be noted that adjacent the inlet end of the body 48*g* there is a tapered section 176 having a plurality of holes therein for permitting the horse to breath when no medication is being supplied, and for admitting air to carry the aerosolized medication to the horse's nostrils. In prior forms of the invention no specific mention was made of air entrance although the structure in FIG. 11 is substantially the same as in FIGS. 14 and 15. In other figures there is simply clearance space around the canister 62, as in well known aerosolization chambers for humans, for example, that shown in the earlier mentioned Foley et al U.S. Pat. No. 5,012,803.

The body is provided with underlying extensions 180 having slots therein for receipt of a strap 182 passing beneath the horse's lower jaw. In addition, there are upward extensions 184 having slots therein for receipt of straps 186 passing over a portion of the harness 36. Further, there are slots 188 adjacent the front of the body for receipt of a connecting strap 190 lying across the front of the horse's muzzle.

G. Seventh Embodiment (FIGS. 17 and 18)

Figure 17:
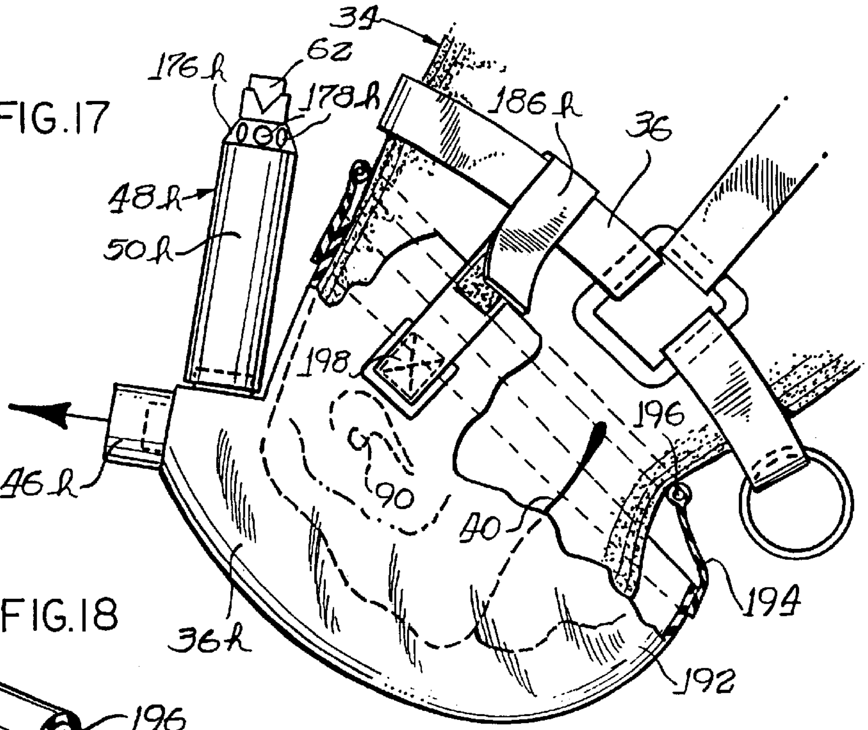
FIG. 17 is a view generally similar to FIG. 10 and showing another embodiment of the invention.
Figure 18:
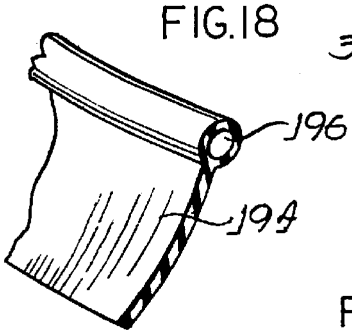
FIG. 18 is a fragmentary view of the seal for the mask.

In the embodiment shown in FIGS. 17 and 18 many of the parts are similar to those previously shown and described, and are identified by like numerals with the addition of the suffix h. A distinction resides in the fact that the mask is made of two pieces, a main body 192 which fits fairly loosely around the horse, and a retaining section 194 suitably secured thereto as by an adhesive. The retaining section 194 is resilient and is provided with a tubular inner edge which fits closely against the horse. Strap 186*h* is mechanically or adhesively secured at 198 to the mask, and passes over a portion of the harness 36.

H. Eighth Embodiment (FIGS. 19 and 20)

Figure 19:
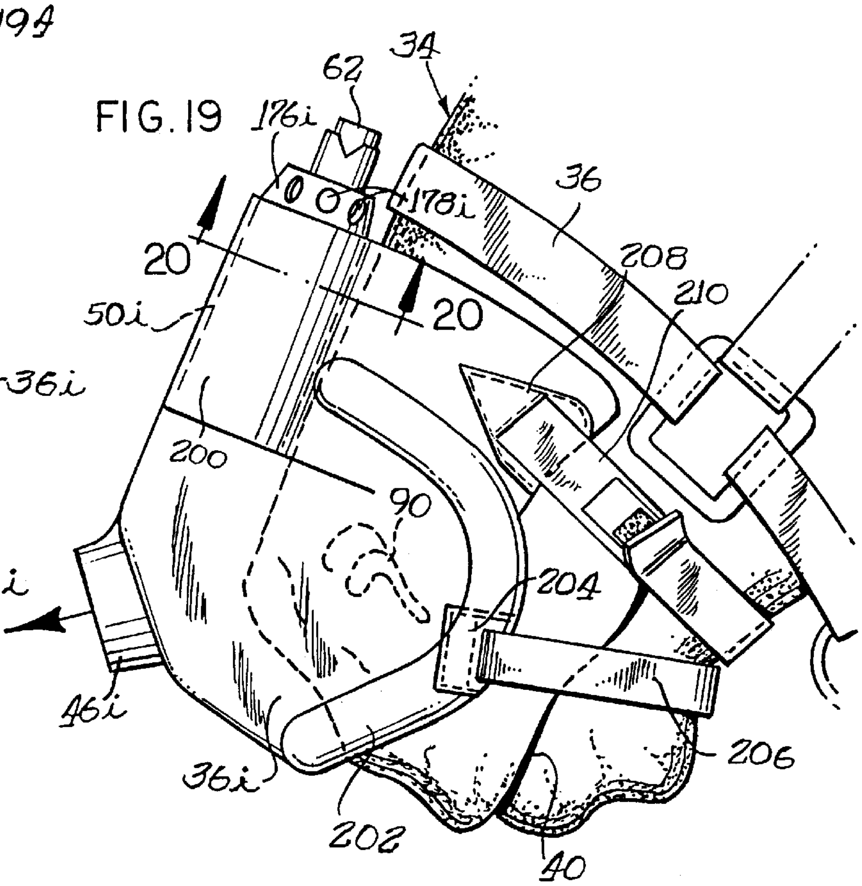
FIG. 19 is a modification of the embodiment of the invention shown in FIG. 14.
Figure 20:
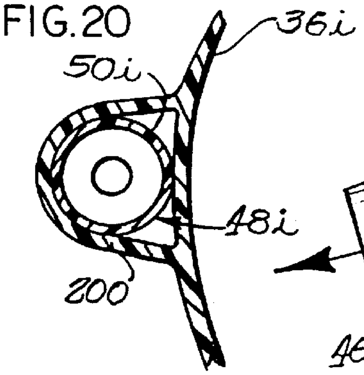
FIG. 20 is a sectional view taken substantially along the line 20—20 in FIG. 19.

Still another embodiment illustrated is that shown in FIGS. 19 and 20. Certain parts are similar to those heretofore shown and described, and are identified by like numerals with the addition of the suffix i. In this instance the mask 36*i* is provided with an extension 200 which houses the aerosolization chamber 48*i.* It opens directly into the mask, which is spaced somewhat above the muzzle of the horse, and in the vicinity of the nostrils 90. A single exhalation valve 46*i* is provided. An extension 202 on the rear or lower portion of the mask has a fixed anchor 204 thereon, and a strap 206 extends beneath the horse's jaw and to a similar anchor on the opposite side.

Another fixed anchor 208 is provided on the lower rear portion of the mask, and a strap 210 extends therefrom to a like anchor on the opposite side. The two straps 206 and 210 hold the mask over the horse's nostrils. Horses are known to be nose or nostril breathers, and hence the coverage of the mouth is not essential.

I. Ninth Embodiment (FIGS. 21 and 22)

Figure 21:
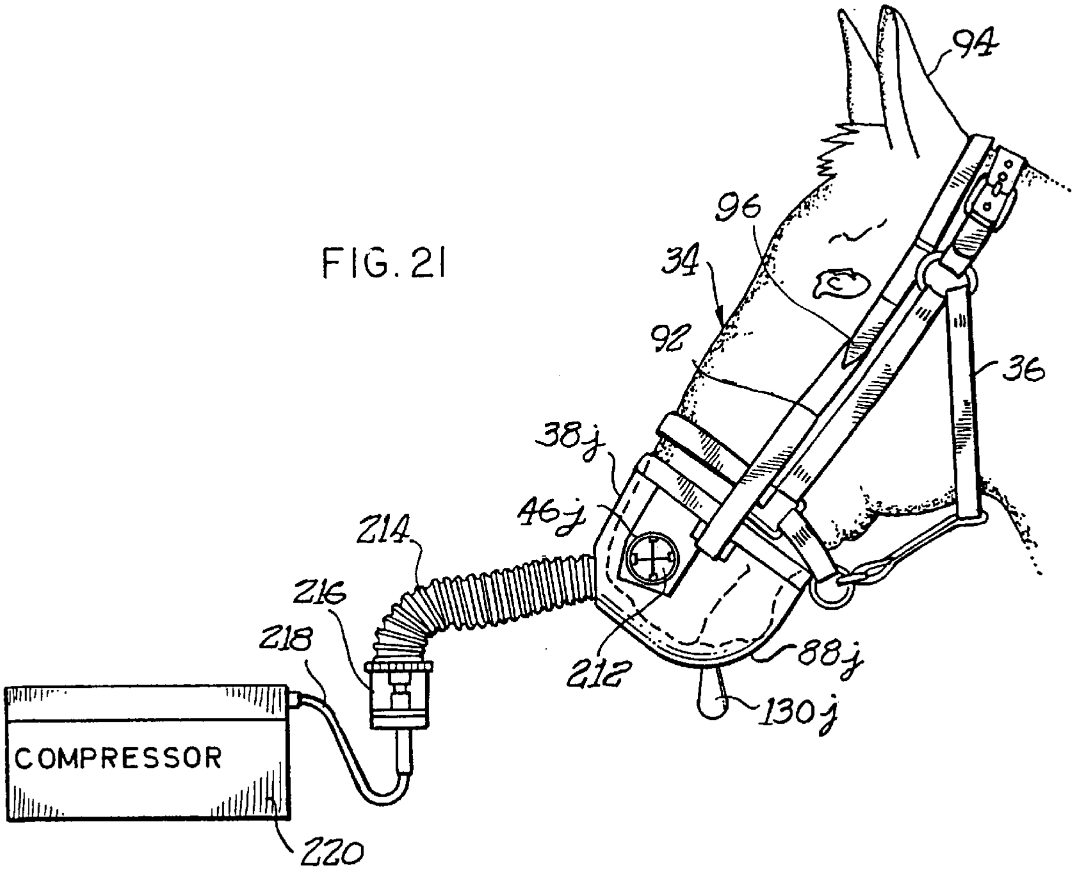
FIG. 21 is a view generally similar to FIG. 6, but showing a modification using a nebulizer rather than a metered dose inhaler.
Figure 22:
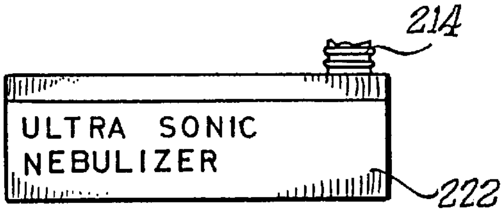
FIG. 22 is a fragmentary view showing a modification of a portion of FIG. 21.

A further embodiment of the invention is shown in FIG. 21 in which a nebulizer is used rather than a metered dose inhaler (MDI). Many of the parts are identical with those heretofore disclosed and are identified by the same numerals. Similar parts are identified by similar numerals with addition of the suffix j.

The mask 38*j* is functionally the same as the mask 38*c* in FIG. 6, and structurally similar thereto. The knob 130*j* has been moved to the slobbering cup area 88*j* where is somewhat more accessible. The exhalation parts or one-way exhalation valve 46*j* are drawn somewhat differently to show the rubber flap valve 212.

The important distinction is that a corrugated aerosol tube or hose 214 is connected to the front center of the mask 38*j* adjacent the horse's nostrils. The inlet or upstream end of the tube or hose 214 is connected to and supplied from a nebulizer 216 which in turn is supplied through a tube 218 with air from an air compressor 220. A few cc of saline solution are placed manually in the nebulizer 216.

Different types of nebulizers are known, and the nebulizer may be any suitable known or conventional type of nebulizer. Indeed, as shown in FIG. 22 an ultrasonic nebulizer 222 may be substituted for the nebulizer 216, the tube 218, and the air compressor 220. The ultrasonic nebulizer 222 is directly connected to the corrugated tube 214.

Considerations Applicable to First Through Ninth Embodiments

Some veterinarians and/or owners are more familiar with aerosolized water (preferably saline) vapor than with aerosolized asthmatic medication from an MDI. Either aerosolized asthmatic medication or aerosolized (saline) water vapor can be considered to be a breathing enhancement vapor, and either can provide a measure of asthmatic relief.

Although certain materials have been suggested for construction of the equine mask, the preferred construction material is a molded acrylic resin. It is substantially rigid, but with a certain flexibility. Further, it is quite strong. This is helpful, in that it is quite possible that the mask could be dropped and stepped on by the horse, and it is desirable that is should not be destroyed by such an accident.

It will be appreciated that standardbred horses and thoroughbred horses, and other breeds tend to be of different sizes, and even individual specimens within a given breed may differ significantly in size. Hence, the mask may have to differ somewhat in size or relative dimensions depending on the horse on which it is to be used. Further, it should be borne in mind that a separate mask should be used for each horse to avoid dangers of cross contamination. Preferably, the entrance area to the mask should be bell shaped, and there should be a "dribble-section" or "slobbering-cup" formed as a part of the bottom of the mask as heretofore noted. Generally speaking, the anti-asthmatic medication can be a beta agonist. Specific forms of anti-asthmatic drugs have been noted heretofore, and it also be noted the corticosteroids are useful in combating asthmatic attacks.

It has been noted that there should not be an air tight seal. The cavities on either side of the horse's mouth soothes the horse as air flows past. With the specific reference to the preferred form of the invention in FIGS. 6–9, the silicone seal was found to work better with the innermost lip or fold 118 pointing in toward the interior of the mask, i.e. toward the end of the horse's muzzle. The mask should create some resistance to breathing for the horse, as this tends to open the airways, allowing for a more effective use of the medication.

Reference has been made to one-way flap valves for the exhalation port. These are not shown in detail, since they are well known, see for example the flap valves in the U.S. patent to Nowacki et al U.S. Pat. No. 4,470,412 and to Foley et al U.S. Pat. No. 5,012,803.

Dead space within the mask is not a major factor, because of the size of the tidal volume of a horse, typically between 3 and 7 liters. A horse's inhalation flow rate is generally between 5 and 10 liters per second. It is preferred to have the aerosolization chamber in a horizontal position, and to have it as low as possible, since the horse will have a tendency to raise its head. Generally speaking, the horse will move its head in a vertical plane, rather than in a horizontal plane. Two breaths of the horse should be allowed between puffs of medication, and the overall time for administering the anti-asthmatic medication is estimated to be in the order of 5 to 10 minutes. It will be apparent that care must be taken in applying the mask so that it does not in any way obstruct the nostrils of the horse. As is known among horse people, it is best to approach a horse from the left side.

It has been noted above that the mask may have to differ in size from one horse to another, and dimensions that have measured by way of example include 5 to 6 inches across the sealing area, with the circumference of this sealing area running from 20 to 23 inches.

The supplying of anti-asthmatic medication to horses is applicable to all types. It will improve the performance of sports horses, such as race horses and jumpers, but it will also improve the performance of working type horses. The embodiments of the invention as herein shown and described will be understood as being exemplary.

J. Tenth Embodiment (FIGS. 23–26)

Figure 23:
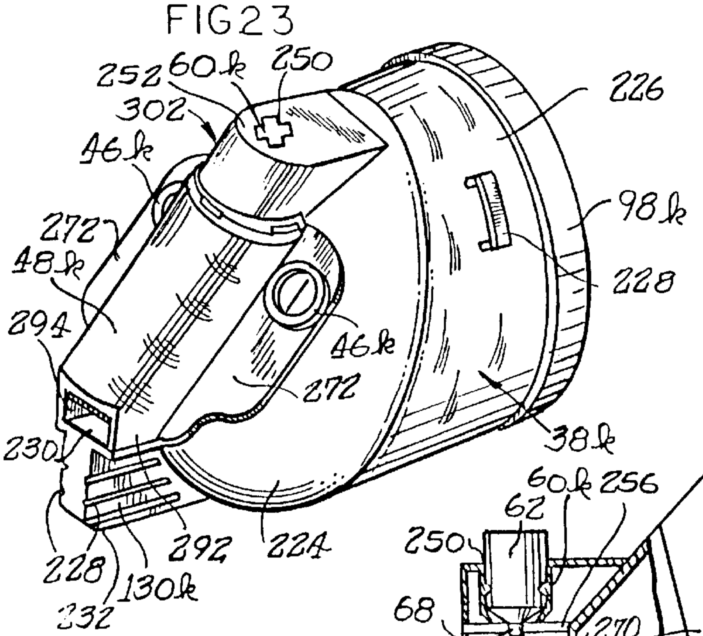
FIG. 23 is a preferred form of the equine mask that has evolved to production status, and comprising a perspective view.

A preferred form of the equine mask has now evolved that is prepared for commercial manufacture. Such mask is shown in FIGS. 23 et seq. The mask is molded of a superior modern plastic. An acrylic plastic is satisfactory for most purposes, and is reasonably inexpensive. However, where hard use is expected such as where the mask might be in a stable or the like where it could be dropped and stepped on by a horse polycarbonate plastic is preferred. In any event, the mask is generally rigid, but is somewhat bendable. In the case of a mask molded of polycarbonate plastic, the plastic will withstand rather considerable deformation without significant damage. The forward part of the mask is clear plastic so that the horse's nostrils, lips, and adjacent parts can be observed by a person administrating medication. The rear portion is cloudy as vision therethrough is not necessary, and helps to focus the attention of the administrating person on the important area of the horse's head. Furthermore, scratches and other marks show less on the cloudy portion. The equine mask now to be described in detail is more durable, repairable, versatile and cleanable.

Figure 24:
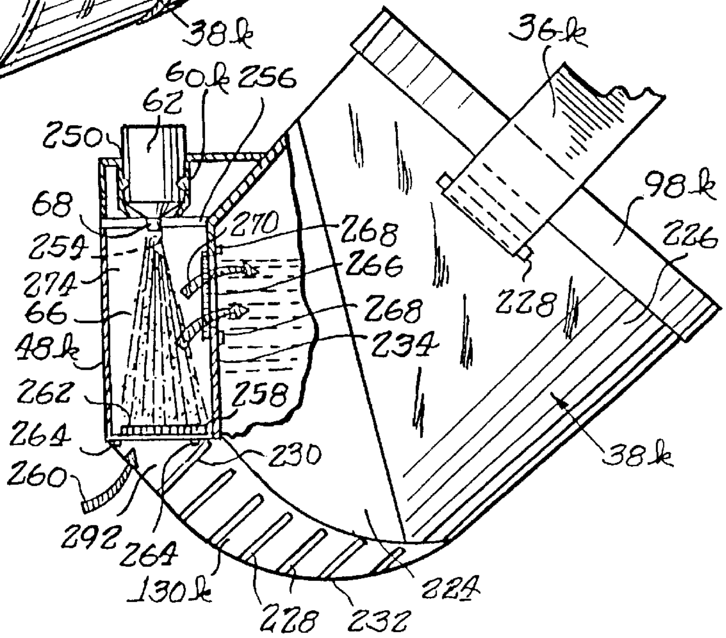
FIG. 24 is a side view of the mask shown in FIG. 23.
Figure 25:
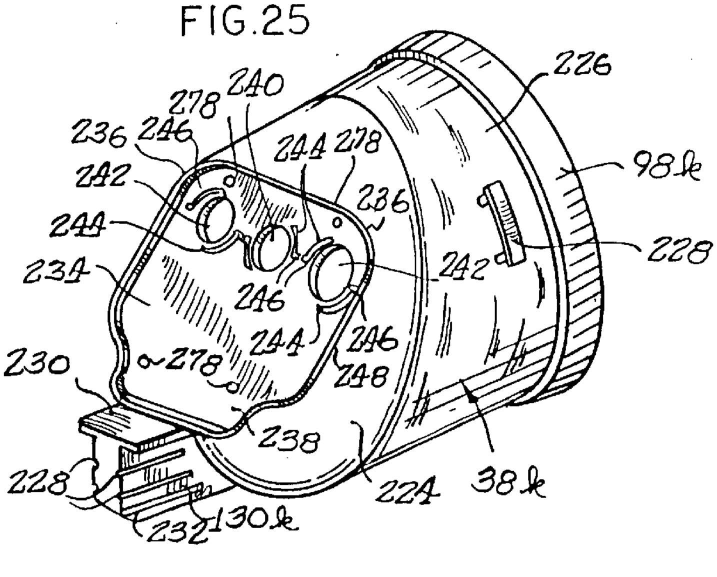
FIG. 25 is a view of a portion of a mask that fits over the front portion of the horse's head, not including the various fittings adaptable thereto.

Turning first to FIGS. 23–25, similar parts are again identified by like numerals, this time with the addition of the suffix k. The mask **38*k* has a gasket 98*k* at the upper or rear portion thereof. The front portion of the mask is clear at 224 so that the horse's nostrils, and preferably also his lips, may be observed while the horse is breathing. The rear portion is cloudy as indicated at 226. The precise areas can vary substantially from those shown in the drawings, and there need not be a definite line of demarcation, although one is indicated in the drawings. There can simply be a fading from the clear portion into the cloudy portion. An integral harness anchoring bar 228 is spaced out from the surface of the mask on either side thereof and generally proximate to the gasket 98*k* for receiving a portion of the harness 36*k* for anchoring the mask on the horse's head. The gasket 98*k* is preferably of the zig-zag rubber type as previously shown and described in FIGS. 6–8 for forming a seal to the horse's head, which both seals and is comfortable to the horse. Alternatively, the gasket or seal could be of the pneumatic type as shown in FIG. 13**. The important thing is that the gasket or seal seals the mask to the horse's head so that there is no leakage to or from the mask. This is important from a medical standpoint, and is also important from an equine behavioral standpoint. Horses are very sensitive to air movement over and along their heads, and a horse could be easily "spooked" by unwanted air movement along the head.

At the lower and frontal portion of the mask there is provided a hand grip **130*k* of hollow box-like formation, having elongated grooves 128 therein extending substantially longitudinally of the hand grip. These grooves afford better gripping for an attendant's hand, and also provide some rigidification if it is assumed that the hand grip 130*k* is hollow. It is not imperative that the hand grip be hollow, but from a weight standpoint it is preferably so. The hand grip is provided along its upper edge with a flange or wall 230 extending outwardly in both directions from the box-like hand grip 228. The hand grip itself lies substantially on a median vertical plane of the mask. The lower front portion 132** of the hand grip is preferably rounded for safe gripping by the trainer or other attendant.

The upper portion of the mask is provided with a planar plate 234 of substantially square configuration, but with rounded upper corners 236, and with a lower tab or tongue portion 238 extending down to the flange or wall 230. The plate 234 is formed integrally with the remainder of the mask, and is provided near the upper portion thereof in horizontally aligned array with a central aperture 240, and two side apertures 242. These apertures are circular in outline, and each is provided outwardly of its perimeter with a pair of arcuate slots 244 having enlarged holes 246 at the lead ends thereof. The entire plate 234 is surrounded by a peripheral, shallow upstanding flange 248.

An aerolization chamber **48*k* is in substantially vertical position when a mask is worn on the front portion of the horse's head. A well 60*k* is disposed above the aerolization chamber 48*k* and opens upwardly through a shaped opening 50 in the top wall 252 above the aerosolization chamber. The entire wall 252 as well as the aerosolization chamber is formed of a resilient plastic, and the shaping of the aperture or opening 250 allows inwardly projecting portions thereof to grip a metered dose inhaler (MDI) 62 with a nozzle 68 thereof extending through an opening 254 in a support member 256 to allow the discharge spray 66 from the cartridge 62 to expand and aerosolize within the chamber 48*k***.

The bottom wall 258 of the chamber **48*k* is spaced somewhat above the wall 200 at the top of the hand gripping piece 130*k* to permit air, as indicated by the arrow 260, to pass between the walls 230 and 258 through a one-way valve 262. The valve has downward projections 264 passing through slots similar to the slots 244 previously mentioned to hold the valve in mounted position over an opening in the bottom wall 258. The structure of the one-way valve will be described more specifically hereinafter, but it is to be understood that it permits air to enter in the direction of the arrow 260**, but not to exit in the opposite direction therefrom.

A similar one-way valve 266 having downward or perpendicular projections 268 thereon is mounted over the hole 240 in the plate 234, by means of projections 268 extending through the enlargement or holes 246 at the end of the slot 244 adjacent the hole 240, the one-way valve then being twisted in a counterclockwise position to lock in place. It will be understood that the projections 268 have enlarged outer ends which pass through the holes 246, and then lock behind the plate 234 to hold the one-way valve in place. The one-way valve 266 permits air and medication to pass into the mask **38*k* in the direction indicated by the arrow 270**.

As will be seen particularly in FIG. 23 the aerosolization chamber **48*k* has wing-like flanges 272 that extend in a common plane, but in opposite directions therefrom, to align in contact with the mounting plate 234, being shaped to fit within the flange 248 about the periphery of the plate 234. The exhalation valves 46*k* are similar to the valves 262 and 266 previously discussed, permitting exhalation of air from the mask, but not permitting entrance of air into the mask upon inhalation. These one-way valves, to be disclosed in detail hereinafter, are provided with extensions or projections which pass through arcuate slots in the flanges 272, and then through the arcuate slots 244, including the enlarged holes 246, in the plate 234, whereby the valves serve not only as one-way exhalation valves, but also as fastening members to secure the flanges 272 and the aerosolization chamber 48*k* in place on the plate 234**.

Figure 26:
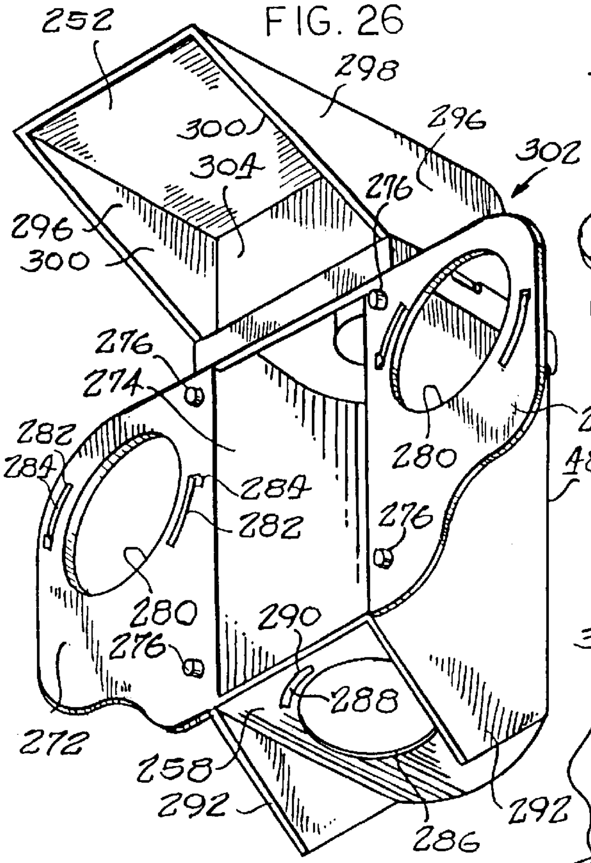
FIG. 26 is a perspective view of a M.D.I. (metered dose inhaler) plate for attachment to the mask.

The aerosolization chamber **48*k* will best be understood with reference to FIG. 26, along with FIGS. 23 and 24. The portion of the aerolization chamber receiving the spray 66 will be seen to be of generally U-shaped outline, providing a cavity 274 into which the spray 274 expands. The wings will be seen to have four pegs 276 extending rearwardly perpendicularly from the wings 272, and respectively received in holes 278 (FIG. 25) in the mounting plate 234. The apertures 280 in the wings 272 which overlie the apertures 242 in the mounting plate 234 in alignment therewith are seen in FIG. 26, along with the arcuate locking slots 282 with the entering end enlargements 284. Similarly, the aperture 286 receiving the inhalation valve 262 is shown in FIG. 26, along with the arcuate locking slots 288 within enlarged entering end 290. Triangular walls 292 depending from the side walls of the aerosolization chamber 48*k* below the bottom wall 258 thereof will be seen to abut the wall 230 at the top of the hand grip 232, defining with this wall a mouth 294 through which air (as indicated by the arrow 260 in FIG. 24) enters to pass through the inhalation valve 262**.

The upper wall 252 is provided with a depending wall 296 on either side thereof which is substantially U-shaped in cross section. A wall 296 has extending triangular sections with terminating edges 300 which lie against the upper to forward portion of the mask for best support of the upper portion 302 which holds the MDI canister 62. A transverse bracing wall 304 may also be provided. Many parts of the aerolization chamber **48*k* will readily be understood as being formed integrally, with other parts such as the raised portion 302** being preferably formed separately and secured to the remainder thereof by any known technique, such as solvent or sonic welding.

Variations of Tenth Embodiment

1. First Variation (FIGS. 27 and 28)

Figure 27:
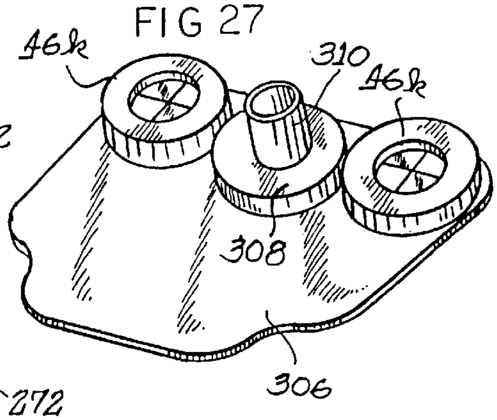
FIG. 27 is perspective view of an adapter plate for securement to the plate shown at the left or front portion of the mask in FIG. 25.
Figure 28:
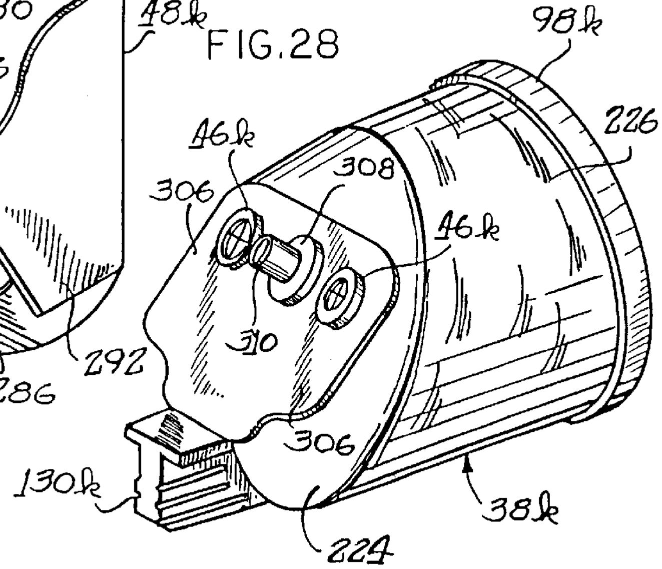
FIG. 28 is a perspective view similar to FIG. 25, with the plate of FIG. 27 mounted thereon.

A variation is shown in FIGS. 27 and 28, in which a plate 306 is secured to the mounting plate 234, previously disclosed. This plate 306 is secured by means of exhalation valves **46*k* as previously discussed in connection with the structure for mounting the aerosolization chamber 48*k*. Rather than the provision of the one-way inhalation valve 266, there is provided a mounting disk 308 secured in the same way to the mounting plate 234 in alignment with the inhalation aperture 240 by means of extending pins having enlargements on the ends thereof, and extending through the mounting slots 244. The mounting disk 308 has a plastic integral tube 310 extending perpendicular to the plate 306. This tube 310 is of proper diameter to accept a conventional corrugated hose for a small volume nebulizer, or an ultrasonic nebulizer, or for oxygen supply. It will be understood that in accordance with the principles of the present invention an aerolization chamber could be provided in combination with a nebulizer or oxygen supply system. As will readily be understood the one-way exhalation valves 46*k* secure the plate 306 to the mounting plate 234** generally as previously described.

2. Second Variation (FIG. 29)

Figure 29:
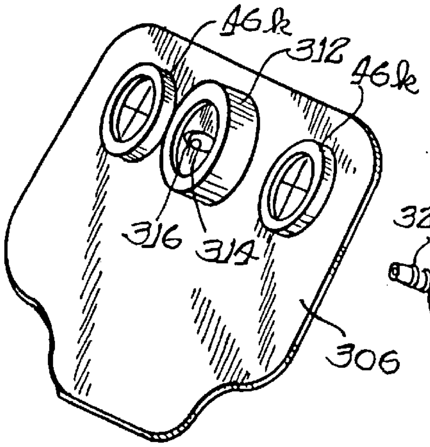
FIG. 29 is a perspective view of an adapter plate generally similar to that in FIG. 27, on a smaller scale, but with a dry powder adapter plate to accept a metered dose dry powder inhaler.

A further modification of the invention is shown in FIG. 29 in which the plate 306 again is provided with the one-way exhalation valves **46*k*, which again mount the plate 306 on the mounting plate 234. A distinction is that a ring 312 mounts on the plate 306 in the same manner as the mounting disk 308 in the embodiment of FIGS. 27 and 28, this ring being spanned by a rubber or plastic membrane 314 having a generally oval or elliptical opening 316** therein for receipt of the exit portion of a metered dose dry powder inhaler.

3. Third Variation (FIG. 30)

Figure 30:
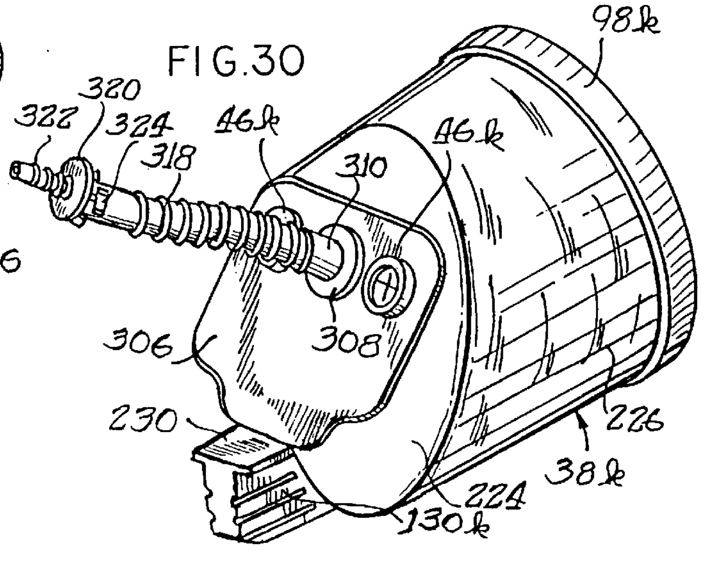
FIG. 30 is a perspective view of a mask with a different adapter plate thereon, specifically an oxygen dilutor unit.

FIG. 30 is generally similar to FIG. 28, and the same numerals are used for identifying parts. The distinction resides in the provision of an oxygen diluter unit comprising a corrugated hose or tubing 318 having a diluter unit 320 at the outer end thereof having an axial oxygen receiving connector 322 at the outer end thereof, and having a lateral window 324 for receiving ambient air. Conventional means is provided for determining the degree of opening or closure of the window 324 to admit diluting air into the oxygen supply through the connector 322.

4. Fourth Variation (FIG. 31)

Figure 31:
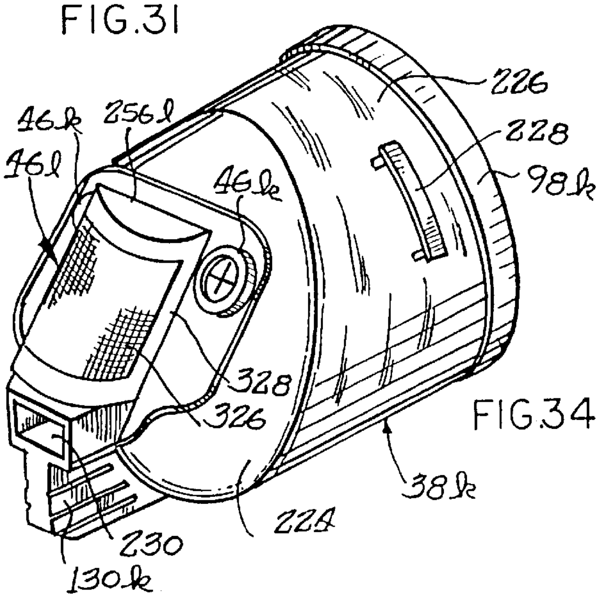
FIG. 31 is a view similar to FIG. 23, but with an air filter plate attached to the mask.

A further modification of the invention is shown in FIG. 31 which superficially resembles FIG. 23. However, in this instance the upper portion 302 is omitted from the chamber 461, the number in this case being modified since the chamber no longer serves the purpose of aerosolization. The top wall 2561 of the chamber is a solid wall, and not apertured for receipt of the nozzle or valve of an MDI canister. Similarly, the bottom wall, although not shown, is also solid or continuous. A replaceable filter 326 is received in an opening 328 in the side wall of the chamber 461 so that the horse may receive filtered air upon inhalation.

Figure 32:
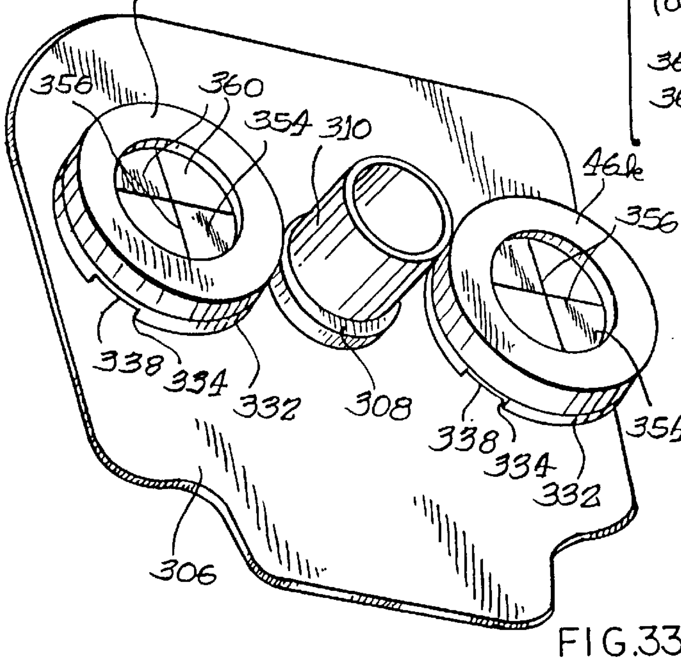
FIG. 32 is a perspective view of an adapter plate generally similar to FIG. 27, but on a somewhat enlarged scale, and showing further details of the exhalation valves.
Figure 34:
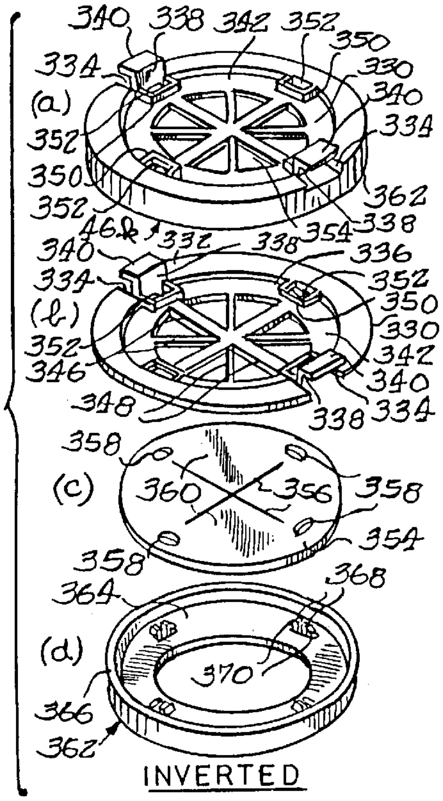
FIG. 34 is an exploded perspective view generally similar to FIG. 33, but with the parts inverted relative to FIG. 33.
Figure 33:
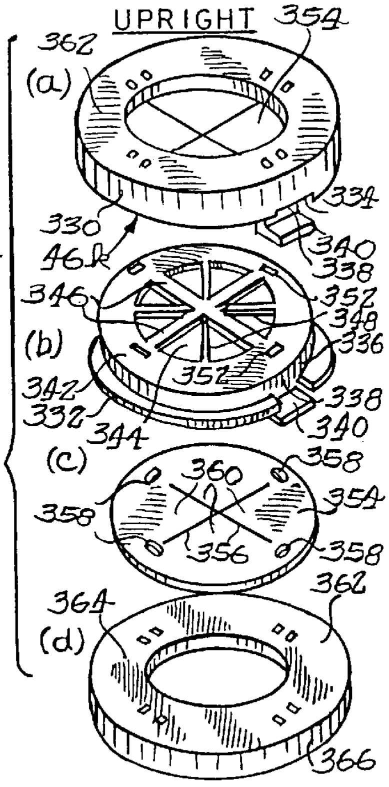
FIG. 33 is an exploded view of the valve just noted in connection with FIG. 32.

Valve Structures of Tenth Embodiment (FIGS. 32–34)

The structure of the one-way valve, exhalation valves **46*k* being chosen for illustration, is shown in detail in FIGS. 32–34. FIG. 32 will be seen to be quite similar to FIG. 27, but from a different angle, and on an enlarged scale to show details of importance. FIG. 32 shows the exhalation valves as assembled on the plate 306. FIG. 33 is an upright view of an exhalation valve 46*k*, FIG. 33**(*a*) being an assembled view of the valve, while FIGS. 33(*b*), 33(*c*) and 33(*d*) are exploded views. FIG. **34*a* is another assembled view of the valve 46*k*, but in inverted position. FIGS. 34*b*, 34*c*, and 34*d* are similar to FIGS. 33*b*, 33*c*, and 34*d*,** but with the parts in relatively inverted position.

The exhalation valve **46*k* consists of three parts joined together to act as a functional entity. The first or base part comprises a spider 333, which includes a peripheral ring or flange 332 relieved at two locations 334 which are 180° apart. An annular flange 336 upstands from the inner edge of the ring 332, and a pair of locking legs 338 depend below the ring 332 and are provided with outwardly directed feet 340. The feet are parallel to the ring 332, and both the legs 338 and the feet 340 are of substantially the same arcuate extents as the gaps 334 in the ring 332**.

A flat ring 342 tops the arcuate wall 336, and extends inwardly therefrom. The ring 342 is provided with a large central aperture 344 which is bridged by two right angle backup arms, and by two narrower arms 348 which are at right angles to one another, but at 45° angles to the relatively wider arms 346. All of the arms are coplaner with the ring 342. Finally, depending walls 350 underlying the ring 342, and cooperating with the ring 332 in the same plane thereas define rectangular areas with arcuately elongated apertures 352 extending through the ring 342.

All parts of the spider 330 as just described are integrally molded of a suitable plastic resin.

Each exhalation valve **46*k* is of three-piece construction, the spider just described being the first piece. The second piece is a flexible diaphragm 354 which preferably is made of a rubber or plastic material. The diaphragm is provided with right angularly disposed slits 356 disposed diametrically of the diaphragm. The diaphragm is further provided outwardly of the slits 356 with arcuately elongated slots or holes 358 through the diaphragm. As best may be seen by comparison of FIGS. 33*b* and 33*c* the diaphragm lies flat on top of the spider 330, particularly the upper ring 342 thereof. The holes 358 in the diaphragm align with the holes 352 in the ring 342, and the slits 356 overlie and are centered on the relatively wide arms 346 of the spider. The narrower arms 348 are centered beneath and support the flaps 360 of the diaphragm defined by the slits 356**.

A third and final part of the exhalation valve comprises a cap 362 including a horizontal, flat ring 364 and a depending peripheral wall 366. This peripheral wall and the periphery of the spider ring 332 may be axially lined or knurled to facilitate gripping and twisting thereof. The cap further includes four pairs of depending studs or legs 368 having outwardly directed teeth 370 with inclined lower faces. The sets of teeth are disposed at 90° to one another, and hold the three parts of the valve together. The diaphragm 354 is laid on top of the spider as noted before, with the apertures 358 therein aligned with the apertures 352 of the spider, and the slits 356 centered on the relatively wide arms 346. The cap 362 then is positioned over the diaphragm and spider, and pressed down. The pairs of legs 368 pass through diaphragm holes 358 and snap through the holes 352 in the spider ring 342, and snap out beneath this ring to hold the three parts in assembled relation.

The exhalation valves are installed by inserting the feet 340 through the enlargements, for example the enlargements 284 in the flanges 272 (FIG. 26), and also through the enlargements 246 of the slots 244 of the mounting plate 234 (FIG. 25), and then twisting the valves. The valves thus are used for assembling the replaceable parts, such as the aerosolization chamber, etc. of FIGS. 23, 24 and 16, or the adapting plates 306 of FIGS. 27–30, and they also serve as the necessary one-way exhalation valves. As will be apparent, the diaphragm flaps 354 are free to flex outwardly away from the spider 330, but cannot flex inwardly because of the relatively wide arms 346 underlying the slits 356, and the relatively narrow arms 348 underlying the flexible flaps of the diaphragm. Not only are the valves dual purpose in permitting exhalation, and in holding parts together, but they are readily removable for cleaning (note that the horse will exhale vapor and mucus thereon) or for substitution of parts, such as the plate 306 for the aerosolization chamber, or for repair, such as replacement of a diaphragm.

The inhalation valves are similar to the exhalation valves, but have the position of the spider and the diaphragm reversed to permit inward air flow, but to prevent outward air flow.

The mask as shown and described in connection with FIGS. 23–34 is molded of a suitable plastic material, as heretofore noted. An acrylic resin is satisfactory for most purposes, although a polycarbonate resin is stronger and more resilient, and would be preferably for use in stable where the mask might be knocked to the ground and stepped on. The mask may vary quite considerably in size in different models depending on the horse with which it is to be used, and for one specific illustration the distance from the front of the handle or hand grip portion 232 to the back of the seal or gasket **98*k* is 7 inches, the top to bottom dimension across the seal is 8 inches, and the lateral dimension across the mounting plate 234** is 5 inches. The rubber seal provides a considerable adaptability, whereby only a few sizes of mask should be necessary to accommodate a large number of horses, with no requirement for an individual size for each horse. The clear or transparent forward position of the mask is advantageous as the technician may watch the horse's nostrils for discharge of medication into the aerosolization chamber toward the end of exhalation and before the start of inhalation. As heretofore noted, various other devices may be applied in place of the aerosolization chamber due to the dual use of the exhalation valves.

Various changes in specific structure will no doubt occur to those skilled in the art, and will be understood as forming a part of the present invention, insofar as they fall within the spirit and the scope of the appended claims.

The invention is claimed as follows:

1. An improved therapy delivery system for horses, for use with (a) a source for providing an aerosol of medication;

(b) an aerosolization holding device having:

(i) a closed chamber;

(ii) an inlet for receiving the aerosol of medication from said source into said chamber;

(iii) an exit passage through which said aerosol can exit said chamber; and (iv) an exit valve located in said exit passage to permit flow in a direction from said chamber and prevent flow into said chamber through said exit passage;

wherein the improvement comprises:

an equine mask comprised of:

(a) a mask body sized and adapted to conform to a forward portion of a head of a horse and to cover at least a horse's nostrils;

(b) a fitting defined around an opening through said mask an inlet communicating with the exit passage of the aerosolization chamber;

(c) an exhalation valve in an opening through said mask, said exhalation valve adapted to permit air flow through said opening upon exhalation into said mask so as to permit a horse wearing said mask to exhale air through said opening, and to prevent air flow through said opening upon inhalation.

2. An equine mask comprising:

a mask body (38*k*) sized and adapted to conform to a forward portion of a head of a horse to cover at least the horse's nostrils;

a chamber (46*k*) adjacent said mask body (38*k*), said chamber having a support wall (256) with an opening (254) through which a source of aerosol is provided, a wall (258) having a one-way valve (262) located in an opening therein, said chamber (46*k*) communicating with said mask body (38*k*) via an opening (240) in a plate (234) thereof;

first and second exhalation valves (46*k*) located in openings (242) through said mask body (38*k*), said openings (242) adjacent the horse's nostrils, said first and second exhalation valves (46*k*) adapted to prevent air flow in a direction from outside said mask body (38*k*) into said mask body (38*k*) through said openings (242), but permit air flow from inside said mask body (38*k*) out of said mask body (38*k*) through said openings (242); and a gasket (98*k*) located along a rear edge (226) of said mask body (38*k*).

3. The equine mask of claim 2 wherein said opening (240) comprises the only inlet through which ambient air can enter into said mask body (38*k* ).

4. The equine mask of claim 2 wherein said openings (242) comprise first and second openings, wherein said first of said openings (242) is located on one side of said opening (240) and adjacent one of the horse's nostrils and said second of said openings (242) is located opposite from said first opening on another side of said opening (240) adjacent the other of the horse's nostrils.

5. The equine mask of claim 2 further including:

wherein said gasket (98*k*) comprises a close fitting seal whereby leakage of air into said mask body (38*k*) except through said opening (240) is reduced.

6. The equine mask of claim 2 wherein said mask body (38*k*) is transparent.

7. An equine mask comprising:

a mask body sized and adapted to conform to a forward portion of a head of a horse covering at least the horse's nostrils;

a mask inlet communicating with a source of aerosol medication and also comprising a means for providing breathing air to the horse, wherein said mask inlet comprises the only inlet into said mask body;

a one-way inhalation valve located with respect to said mask inlet to prevent flow of air from said mask body; and first and second exhalation valves located in openings through said mask body, said openings adjacent the horse's nostrils, said first and second exhalation valves adapted to prevent air flow in a direction from outside said mask body into said mask body through said openings, but permit air flow from inside said mask body out of said mask body through said openings.

8. The equine mask of claim 7 wherein said mask inlet comprises the only inlet into said mask body.

9. The invention of claim 7 wherein said openings comprise first and second openings, wherein said first of said openings is located on one side of said mask inlet and adjacent one of the horse's nostrils and said second of said openings is located opposite from said first opening on another side of said mask inlet and adjacent the other of the horse's nostrils.

10. The invention of claim 7 further including:

a close fitting gasket located along a rear edge of said mask body and conforming in shape to a horse's head, whereby leakage of air into said mask body except through said mask inlet is reduced.

11. The invention of claim 7 wherein said mask body is transparent.

12. An equine mask comprising:

a mask body sized and adapted to conform to a forward portion of a head of a horse to cover at least the horse's nostrils;

a mask inlet communicating with a source of aerosol medication, wherein said mask inlet comprises the only inlet into said mask body;

a one-way inhalation valve located in said mask inlet to prevent flow of air from said mask body into said source of aerosol medication;

first and second openings located through said mask body, wherein said first of said openings is located on one side of said mask inlet adjacent one of the horse's nostrils and said second of said openings is located opposite from said first opening on another side of said mask inlet adjacent the other of the horse's nostrils; and a first exhalation valve located in said first opening through said mask body and a second exhalation valve located in said second opening through said mask body, said first and second exhalation valves adapted to prevent air flow in a direction from outside said mask body into said mask body through said openings, but permit air flow from inside said mask body out of said mask body through said openings.

13. The invention of claim 12 further including:

a close fitting gasket located along a rear edge of said mask body and conforming in shape to a horse's head, whereby leakage of air into said mask body except through said mask inlet is reduced.

14. The invention of claim 12 wherein said mask body is transparent.

15. An equine mask comprising:

a mask body sized and adapted to conform to a forward portion of a head of a horse and to cover at least the horse's nostrils;

a first opening providing an air inlet into said mask body;

a one-way inhalation valve located with respect to said first opening to prevent flow of air from inside said mask body through said one-way inhalation valve;

a means for providing aerosol medication from a source thereof to said mask body, said providing means comprising a second inlet through which an aerosol can be provided to said first opening; and first and second exhalation valves located in third and fourth openings through said mask body, said third and fourth openings adjacent the horse's nostrils, said first and second exhalation valves adapted to prevent air flow in a direction from outside said mask body into said mask body through said openings, but to permit air flow from inside said mask body out of said mask body through said openings.

16. The invention of claim 15 wherein said third opening is located on one side of said mask inlet adjacent one of the horse's nostrils and said fourth opening is located opposite from said third opening on another side of said mask inlet adjacent the other of the horse's nostrils.

17. The equine mask of claim 15 wherein said mask inlet comprises the only inlet into said mask body.

18. The invention of claim 15 further including:

a close fitting gasket located along a rear edge of said mask body and conforming in shape to a horse's head, whereby leakage of air into said mask body except through said mask inlet is reduced.

19. The invention of claim 15 wherein said mask body is transparent.

* * * * *

UNITED STATES PATENT AND TRADEMARK OFFICE

CERTIFICATE OF CORRECTION

PATENT NO. : 5,954,049 — Page 1 of 1
DATED : September 21, 1999
INVENTOR(S) : Martin P. Foley et al.

It is certified that error appears in the above-identified patent and that said Letters Patent is hereby corrected as shown below:

Title page

Column 1,
Item [75], after "London," insert -- Ontario --.

Column 2,
Line 3, under "FOREIGN PATENT DOCUMENTS", delete "815329" and substitute -- 812329 -- in its place.
Line 9, under "ABSTRACT", delete "animals" and substitute -- animal's -- in its place.

Signed and Sealed this

Fourteenth Day of August, 2001

*Attest:*

Nicholas P. Godici

NICHOLAS P. GODICI

*Attesting Officer* — *Acting Director of the United States Patent and Trademark Office*